(12) United States Patent
Bingham et al.

(10) Patent No.: US 11,878,147 B2
(45) Date of Patent: Jan. 23, 2024

(54) NEEDLE-LESS INJECTOR AND METHOD OF FLUID DELIVERY

(71) Applicant: PharmaJet, Inc., Golden, CO (US)

(72) Inventors: John Bingham, Elizabeth, CO (US); Robert Steinway, Boulder, CO (US)

(73) Assignee: PharmaJet Inc., Golden, CO (US)

( * ) Notice: Subject to any disclaimer, the term of this patent is extended or adjusted under 35 U.S.C. 154(b) by 494 days.

(21) Appl. No.: 17/160,036

(22) Filed: Jan. 27, 2021

(65) Prior Publication Data

US 2021/0146051 A1 May 20, 2021

Related U.S. Application Data

(63) Continuation of application No. 16/113,133, filed on Aug. 27, 2018, now abandoned, which is a
(Continued)

(51) Int. Cl.
*A61M 5/30* (2006.01)
*A61M 5/315* (2006.01)
(Continued)

(52) U.S. Cl.
CPC ............ *A61M 5/30* (2013.01); *A61M 5/3158* (2013.01); *A61M 5/002* (2013.01); *A61M 5/425* (2013.01);
(Continued)

(58) Field of Classification Search
CPC .... A61M 2005/208; A61M 2205/6081; A61M 5/002; A61M 5/30; A61M 5/3158; A61M 5/425
See application file for complete search history.

(56) References Cited

U.S. PATENT DOCUMENTS

| | | | |
|---|---|---|---|
| 569,887 | A | 10/1896 | Richardson |
| 2,547,099 | A | 4/1951 | Smoot |

(Continued)

FOREIGN PATENT DOCUMENTS

| | | |
|---|---|---|
| CA | 569887 | 2/1959 |
| CA | 2430449 | 11/2003 |

(Continued)

OTHER PUBLICATIONS

International Search Report dated Jun. 15, 2006, for PCT Patent Application No. PCT/US05/46041 filed on Dec. 20, 2005, one page.
(Continued)

*Primary Examiner* — Quynh-Nhu H. Vu
(74) *Attorney, Agent, or Firm* — Quarles & Brady LLP (57) ABSTRACT

A method and system of providing a needle-less injector specifically configured to the needs of a user. The method includes assembling a needle-less injector by positioning an inner housing within the outer housing such that the inner housing is axially movable within the outer housing between a ready position and a firing position. The method further includes receiving a user selection of a delivery spring weight from a plurality of available delivery spring weights. Then a delivery spring having the selected spring weight is placed within the inner housing. The completed needle-less injector having a delivery spring with the selected weigh may then be delivered to the user. In alternative injector configurations, the user may also select one or more of a skin tensioning spring weight or a hammer length along with or instead of the delivery spring weight.

12 Claims, 10 Drawing Sheets

Related U.S. Application Data continuation of application No. 15/139,981, filed on Apr. 27, 2016, now Pat. No. 10,099,011, which is a continuation of application No. 14/019,202, filed on Sep. 5, 2013, now Pat. No. 9,333,300, which is a continuation of application No. 13/162,302, filed on Jun. 16, 2011, now Pat. No. 8,529,500, which is a continuation of application No. 12/575,394, filed on Oct. 7, 2009, now abandoned, which is a continuation of application No. 11/598,193, filed on Nov. 13, 2006, now Pat. No. 7,618,393.

(51) Int. Cl.
A61M 5/00 (2006.01)
A61M 5/42 (2006.01)
A61M 5/20 (2006.01)

(52) U.S. Cl.
CPC ............... A61M 2005/208 (2013.01); A61M 2205/6081 (2013.01)

(56) References Cited

U.S. PATENT DOCUMENTS

| | | | |
|---|---|---|---|
| 2,605,763 A | 8/1952 | Smoot | |
| 2,635,601 A | 4/1953 | May | |
| 2,645,223 A | 7/1953 | Lawshe et al. | |
| 2,687,724 A | 8/1954 | Ziherl et al. | |
| 2,699,166 A | 1/1955 | Dickinson, Jr. et al. | |
| 2,704,542 A | 3/1955 | Scherer | |
| 2,704,543 A * | 3/1955 | Scherer | A61M 5/30 604/68 |
| 2,737,946 A | 3/1956 | Hein, Jr. | |
| 2,764,977 A | 10/1956 | Ferguson | |
| 2,800,903 A | 7/1957 | Smoot | |
| RE24,419 E | 1/1958 | Ziherl et al. | |
| 2,821,193 A | 1/1958 | Ziherl et al. | |
| 2,821,981 A | 2/1958 | Ziherl et al. | |
| 3,057,349 A | 10/1962 | Ismach | |
| 3,115,133 A | 12/1963 | Morando | |
| 3,131,692 A | 5/1964 | Love | |
| 3,138,157 A | 6/1964 | Ziherl et al. | |
| 3,202,151 A | 8/1965 | Kath | |
| 3,292,621 A | 12/1966 | Banker | |
| 3,292,622 A | 12/1966 | Banker | |
| 3,335,722 A | 8/1967 | Lowry et al. | |
| 3,424,154 A | 1/1969 | Kinsley | |
| 3,461,867 A | 8/1969 | Zimmet et al. | |
| 3,540,444 A | 11/1970 | Moreland | |
| 3,688,765 A | 9/1972 | Gasaway | |
| 3,695,266 A | 10/1972 | Lussier | |
| 3,714,943 A | 2/1973 | Yanof et al. | |
| 3,763,359 A | 10/1973 | Cho et al. | |
| 3,763,859 A | 10/1973 | Yanof et al. | |
| 3,788,315 A | 1/1974 | Laurens | |
| 3,805,783 A | 4/1974 | Ismach | |
| 3,815,594 A | 6/1974 | Doherty | |
| 3,853,125 A | 12/1974 | Clark et al. | |
| 3,859,996 A | 1/1975 | Mizzy et al. | |
| 3,908,651 A | 9/1975 | Fudge | |
| 3,933,155 A | 1/1976 | Johnston | |
| 3,945,379 A | 3/1976 | Pritz et al. | |
| 3,945,383 A | 3/1976 | Bennett et al. | |
| 4,004,575 A | 1/1977 | Sarstedt | |
| 4,031,889 A | 6/1977 | Pike | |
| 4,059,107 A | 11/1977 | Iriquchi et al. | |
| 4,089,334 A | 5/1978 | Schwebel et al. | |
| 4,103,684 A | 8/1978 | Ismach | |
| 4,124,024 A | 11/1978 | Schwebel | |
| 4,128,098 A | 12/1978 | Bloom et al. | |
| 4,301,795 A | 11/1981 | Zimmerman | |
| 4,329,988 A | 5/1982 | Sarnoff et al. | |
| 4,342,310 A | 8/1982 | Lindmayer et al. | |
| 4,400,172 A | 8/1983 | Dettbarn et al. | |
| 4,403,609 A | 9/1983 | Cohen | |
| 4,403,989 A | 9/1983 | Christensen et al. | |
| 4,421,508 A | 12/1983 | Cohen | |
| 4,447,225 A | 5/1984 | Taff et al. | |
| 4,475,905 A | 10/1984 | Himmelstrup | |
| 4,507,113 A | 3/1985 | Dunlap | |
| 4,518,385 A | 5/1985 | Lindmayer et al. | |
| 4,592,742 A | 6/1986 | Landau | |
| 4,596,556 A | 6/1986 | Morrow et al. | |
| 4,623,332 A * | 11/1986 | Lindmayer | A61M 5/30 604/68 |
| 4,680,027 A | 7/1987 | Parsons et al. | |
| 4,722,728 A * | 2/1988 | Dixon | A61M 5/30 604/68 |
| 5,106,371 A | 4/1992 | Zhao et al. | |
| 5,211,628 A | 5/1993 | Marshall | |
| 5,312,335 A | 5/1994 | McKinnon et al. | |
| 5,312,348 A | 5/1994 | Sans | |
| 5,397,313 A | 3/1995 | Gross | |
| 5,499,972 A | 3/1996 | Parsons | |
| 5,503,627 A | 4/1996 | McKinnon et al. | |
| 5,527,284 A | 6/1996 | Ohnemus et al. | |
| 5,531,705 A | 7/1996 | Alter et al. | |
| 5,556,384 A | 9/1996 | de Encarnacao | |
| 5,569,189 A | 10/1996 | Parsons | |
| 5,569,203 A | 10/1996 | Chen | |
| 5,575,774 A | 11/1996 | Chen | |
| 5,578,015 A | 11/1996 | Robb | |
| 5,599,302 A | 2/1997 | Lilley et al. | |
| 5,620,423 A | 4/1997 | Eykmann et al. | |
| 5,649,912 A | 7/1997 | Peterson | |
| 5,704,911 A | 1/1998 | Parsons | |
| 5,782,802 A * | 7/1998 | Landau | A61M 5/30 604/72 |
| 5,865,795 A | 2/1999 | Schiff et al. | |
| 5,891,086 A | 4/1999 | Weston | |
| 5,899,879 A | 5/1999 | Umbaugh | |
| 5,993,412 A | 11/1999 | Deily et al. | |
| 6,053,895 A | 4/2000 | Kolberg et al. | |
| 6,083,197 A | 7/2000 | Umbaugh | |
| 6,123,684 A * | 9/2000 | Deboer | A61M 5/30 604/134 |
| 6,224,577 B1 | 5/2001 | Dedola et al. | |
| 6,319,224 B1 | 11/2001 | Stout et al. | |
| 6,398,763 B1 | 6/2002 | Richardson et al. | |
| 6,506,177 B2 | 1/2003 | Landau | |
| 6,558,348 B2 | 5/2003 | Parsons | |
| 6,673,035 B1 | 1/2004 | Rice et al. | |
| 6,942,638 B1 * | 9/2005 | Quinn | A61M 5/31513 604/222 |
| 7,235,063 B2 | 6/2007 | D'Antonio et al. | |
| 7,442,182 B2 | 10/2008 | Landau et al. | |
| 7,618,393 B2 | 11/2009 | Bingham et al. | |
| 7,699,802 B2 | 4/2010 | Steinway et al. | |
| 8,529,500 B2 | 9/2013 | Bingham et al. | |
| 9,333,300 B2 | 5/2016 | Bingham et al. | |
| 10,099,011 B2 | 10/2018 | Bingham et al. | |
| 2001/0031945 A1* | 10/2001 | Haar | A61M 5/30 604/134 |
| 2001/0031956 A1 | 10/2001 | Drevik | |
| 2002/0022806 A1 | 2/2002 | Witowski | |
| 2002/0188251 A1 | 12/2002 | Staylor et al. | |
| 2003/0040715 A1 | 2/2003 | D'Antonio et al. | |
| 2003/0065286 A1 | 4/2003 | Landau | |
| 2003/0132547 A1 | 7/2003 | Heffernan et al. | |
| 2003/0225368 A1 | 12/2003 | Landau et al. | |
| 2004/0134563 A1 | 7/2004 | Rice | |
| 2004/0159364 A1 | 8/2004 | Landau et al. | |
| 2004/0186437 A1 | 9/2004 | Frenette et al. | |
| 2005/0209554 A1* | 9/2005 | Landau | A61M 5/30 604/72 |
| 2006/0089593 A1* | 4/2006 | Landau | A61M 5/30 604/110 |
| 2006/0089594 A1 | 4/2006 | Landau et al. | |
| 2006/0106362 A1* | 5/2006 | Pass | A61M 5/30 604/68 |
| 2007/0027428 A1 | 2/2007 | Bingham | |
| 2007/0118094 A1 | 5/2007 | Bingham et al. | |

(56) References Cited

U.S. PATENT DOCUMENTS

| | | | |
|---|---|---|---|
| 2007/0191762 A1* | 8/2007 | Quinn | A61M 5/30 604/68 |
| 2008/0228147 A1 | 9/2008 | David-Hegerich et al. | |
| 2009/0156992 A1 | 6/2009 | Landau | |
| 2010/0168662 A1 | 7/2010 | Bingham et al. | |
| 2016/0235917 A1 | 8/2016 | Bingham et al. | |
| 2018/0361070 A1 | 12/2018 | Bingham et al. | |

FOREIGN PATENT DOCUMENTS

| | | |
|---|---|---|
| EP | 1 093 826 | 4/2001 |
| WO | WO-95-03844 | 2/1995 |
| WO | WO-97-36783 | 10/1997 |
| WO | WO-02-05878 | 1/2002 |
| WO | WO-2004-041331 | 5/2004 |
| WO | WO-2006-106291 | 10/2006 |
| WO | WO-2006-118616 | 11/2006 |
| WO | WO-2007-146266 | 12/2007 |
| WO | WO-2008-063995 | 5/2008 |

OTHER PUBLICATIONS

International Search Report dated Oct. 11, 2007, for PCT Patent Application No. PCT/US2007/013744 filed on Jun. 12, 2007, three pages.
International Search Report dated Jul. 23, 2008, for PCT Patent Application No. PCT/US2007/84510 filed Nov. 13, 2007, six pages.
Supplementary Partial European Search Report dated Jul. 23, 2008, for EP Patent Application No. 05854705.0 filed Dec. 12, 2005, seven pages.

\* cited by examiner

NEEDLE-LESS INJECTOR AND METHOD OF FLUID DELIVERY

RELATED APPLICATIONS

The present application is a continuation of pending U.S. patent application Ser. No. 16/113,133 entitled "Needle-Less Injector and Method of Fluid Delivery," filed on Aug. 27, 2018, which is a continuation of U.S. application Ser. No. 15/139,981 (now U.S. Pat. No. 10,099,011) entitled "Needle-Less Injector and Method of Fluid Delivery," filed on Apr. 27, 2016, which is a continuation of U.S. application Ser. No. 14/019,202 (now U.S. Pat. No. 9,333,300), entitled "Needle-Less Injector and Method of Fluid Delivery," filed on Sep. 5, 2013, which is a continuation of U.S. patent application Ser. No. 13/162,302 (now U.S. Pat. No. 8,529,500), entitled "Needle-less Injector and Method of Fluid Delivery," filed on Jun. 16, 2011, which is a continuation of U.S. patent application Ser. No. 12/575,394, entitled "Needle-Less Injector and Method of Fluid Delivery," filed on Oct. 7, 2009, which is a continuation of U.S. patent application Ser. No. 11/598,193 (now U.S. Pat. No. 7,618,393), entitled "Needle-less Injector and Method of Fluid Delivery," filed on Nov. 13, 2006, each of which is hereby incorporated by reference in its entirety.

BACKGROUND OF THE INVENTION

1. Field of the Invention

The present invention relates to a needle-less injector that can deliver a high-pressure jet of fluid, such as a medicament, intramuscularly, intradermally and/or subcutaneously into the tissue a human or animal, and more particularly to a method of delivering a specific dose of medicament via a needle-less injector.

2. Description of Related Art

The advantages of needle-less injection devices have been recognized for some time. Some of these advantages include: the absence of needle stick injuries that present hazards to healthcare workers; a reduction in the risk of cross-contamination among patients, whether, human or animal; the elimination of needle breakage in the tissue of the human or animal; and that the jet of liquid medicament is generally smaller than the diameter of a hypodermic needle and thus may be less invasive than a hypodermic needle.

Because of the well-known advantages of needle-less injection, there are many different kinds of such devices, including pneumatic needle-less injection devices that are designed to provide multiple doses to patients or animals, or gas actuated, which are for single or multiple use. Most known needle-less injection devices operate by using a piston to drive the fluid to be delivered though a fine nozzle that creates a small, high pressure stream that penetrates the skin simply due to the high pressure. Multi-dose and single-dose devices depend on a source of energy to drive air or working fluid that is used to operate the piston that drives the fluid through the nozzle. Thus, a serious limitation of these devices is that they must have a readily available source of energy to drive the piston. This makes these devices impractical for use in hospitals and/or clinics, and in most field situations, especially in remote areas where access to dependable energy is uncertain.

These injector devices are also large, sometimes expensive units, and generally adapted to retain large quantities of medicament for repeated injections. Most of these machines are not portable and have historically been used chiefly for mass inoculation programs.

Because of the disadvantages of injection devices that use high-pressure fluids to drive the piston and deliver multiple injections, a great deal of attention has been given to the development of a spring-powered needle-less injection device for delivering a single injection. The success of the known devices has been limited, due to problems associated with safety and reliability. The issues regarding safety generally involve the possibility of accidental discharge of the device and the possibility of transmitting diseases between patients due to carryover of body fluids. The problems associated with reliability generally involve the device's ability to deliver a full, known dose of the liquid.

Safety issues generally arise in association with devices that have exposed triggers or include a hammer or piston driving device that can extend beyond the inner housing of the injector. The risk of using this type of device is similar to the risks associated with the triggers on firearms, and that is the inadvertent pressing of the trigger, can result in the accidental or premature firing of the device.

Reliability issues include a broad spectrum of problems. One significant problem is the creation of a suitable jet or stream of fluid and the introduction of this jet on to the skin of the animal or human. Preferably, the jet will be a very fine jet that will impact a section of taut skin at an angle of incidence of preferably 90 degrees. Most of the energy of the stream is used to penetrate the skin when the jet impacts at approximately 90 degrees to the skin. Additionally, by keeping the skin taut prior to delivering the jet of fluid, the skin is not allowed to flex, and thus more of the energy from the jet is used to penetrate the skin rather than deflecting or moving the skin.

Yet another problem associated with needle-less devices is maintenance of a required amount of pressure during the delivery of the medicament from the reservoir, through the nozzle. As disclosed in U.S. Pat. No. 6,942,638, the entirety of which is hereby incorporated by reference, a loss of pressure can affect the amount of medicament delivered.

There are also disadvantages related to the containment of the fluid formulations in single dose needle-less injectors. Individual doses of a liquid formulation can be delivered via the injector. However, often the volume of medicament held in the conventional injectors is too large, for example, when injecting an infant or small animal, such as a mouse. Often one-half or more of the dosage is not required and hence would be wasted or the injection could not be given safely to such patient. This decreases the practicality and use of the injectors in certain environments.

Another problem with medicament containment is that many materials proposed for the vials are unsuitable for long-term contact with the medicament, or at least would require extensive and costly validation for each application.

Another disadvantage of known needle-less injectors is the inability to direct the location of the injection, i.e., intramuscularly, intradermally and/or subcutaneously

SUMMARY OF THE INVENTION

According to one aspect of the present invention there is provided a hand-held, spring-powered, needle-less injector device that can deliver a single dose of liquid, such as a medicament, both safely and reliably without an external power source.

In another aspect, the needle-less injector of the present invent prevents accidental discharge. The needle-less injector device has a trigger stop that prevents operation of the trigger when the inner housing in not in the firing position. An example of this trigger stop includes a protrusion that extends from the outer housing and impedes the movement of the trigger when inner housing is not in the firing position. The protrusion then moves away from the trigger when the inner housing is moved into the firing position.

In yet another aspect, the needle-less injector device of the present invention uses a single-use, disposable needle free syringe containing a liquid for delivery. The syringe includes a connector at one end and a nozzle and skin tensioner at the other end. The connector can be a bayonet type connector. The skin tensioner can be a ridge that surrounds the nozzle. The syringe is easily insertable into the injector and provides for a safer healthcare environment.

It is still another aspect of the present invention to provide a needless injector that can deliver smaller doses of medicament without providing different vial sizes.

Another aspect of the present invention is to provide a needless injector that can control the particular location of the injection, i.e., intramuscularly, intradermally and/or subcutaneously.

During operation of the injector, the user will position the hammer at the cocked position and insert the syringe into the leading end of the inner housing. The syringe can be pre-filled with the liquid that is to be delivered to the animal or human as described above. The user presses the nozzle and skin tensioner against the animal or human, causing the inner housing of the device to move against the skin tensioning spring, into or relative to the outer housing to the firing position. Once the inner housing is moved to the firing position, the pressure of the skin tensioning spring is reacted against the animal or human, causing the skin to be stretched taut across the skin tensioner. This stretching of the skin across the skin tensioner will position the target area of the skin at a right angle to the syringe and the nozzle. The movement of the inner housing to the firing position also results in the movement of a protrusion relative to the inner housing such that the protrusion no longer obstructs the movement of the trigger. The user then simply presses the trigger, which releases the spring driven hammer, which in turn drives the fluid through the nozzle of the syringe and into the animal or human's skin.

The hammer may drive a separate plunger with a seal through the syringe to expel the fluid in the syringe through the nozzle of the syringe. However, the syringe may incorporate portions, or all, of the plunger to deliver different amounts of medicament into the skin.

Still further, it is contemplated that the use of a separate plunger will allow the use of a mechanical cocking device that will push against the hammer to move the hammer from an unloaded position to the cocked position.

According to these and other aspects there is provided a needle-less injector device for delivering a dose of fluid intradermally, subcutaneously or intramuscularly to an animal or human. The device includes an inner housing having opposed ends. A syringe is disposed in one end of the inner housing. The syringe includes a nozzle for delivering a dose of fluid held within the syringe. A plunger is movably disposed within the syringe. A spring powered hammer is movably disposed within the inner housing. The hammer cooperates with the plunger to drive the dose of medicament from the nozzle. An injection delivery spring for powering the hammer is positioned and compressed between the other end of the inner housing and the spring powered hammer. An outer housing slideably supports the inner housing. A skin tensioning spring is mounted between the inner housing and the outer housing, the skin tensioning spring biasing the nozzle of the syringe against the animal or human. A trigger mechanism is disposed in the outer housing, the trigger mechanism cooperating with the spring powered hammer to release the injection delivery spring, wherein the size of the injection delivery spring, skin tensioning spring and the length of the hammer dictate the amount of dose delivered and whether the dose is delivered intradermally, subcutaneously or intramuscularly to an animal or human.

According to these and other aspects there is provided a method for delivering a dose of medicament intradermally, subcutaneously or intramuscularly to an animal or human. The method includes the steps of providing a syringe containing a predetermined dose of medicament, the syringe including a nozzle for delivering the medicament and a skin tensioner, and providing a needle-less injector device. The needle-less injector device includes an inner housing having a leading end and a trailing end, the leading end of the inner housing being adapted for receiving the syringe; a hammer movably disposed within the inner housing; an injection delivery spring disposed in the inner housing between the hammer and the trailing end of the inner housing for driving the hammer; a plunger movably and sealingly located within the syringe, the plunger being driven by the hammer; a hollow outer housing adapted for slideably receiving the inner housing therein, the inner housing being movable within the hollow outer housing between a safe position and a firing position; and a skin tensioning spring mounted between the inner housing and the outer housing, the skin tensioning spring biasing the nozzle toward the skin of the human or animal. When the nozzle of the syringe is placed against the skin, and the trigger is pressed, the hammer is released and the hammer forces the plunger through the syringe to eject the fluid from the syringe through the nozzle into the skin, wherein the size of the injection delivery spring, skin tensioning spring and the length of the hammer dictate the amount of dose delivered and whether the dose is delivered intradermally, subcutaneously or intramuscularly to an animal or human.

These and other objects, features, aspects, and advantages of the present invention will become more apparent from the following detailed description of the preferred embodiment relative to the accompanied drawings, in which:

DETAILED DESCRIPTION OF THE PREFERRED EMBODIMENTS

Referring to FIGS. 1-5, a hand-held, spring-powered, needle-less injector device 10 includes an inner housing 12 having a leading end 14 and a trailing end 16. The leading end 14 of the inner housing 12 is constructed and arranged to receive a vial, ampule or syringe 18 that is used to hold a fluid 20 that is to be delivered through the skin 22 covering tissue of an animal or human 24 and into the tissue thereof. It should be appreciated that although the present invention is described in relation to "skin" and "animal," it is intended to include humans, animals and other surfaces. As will be described further herein, the needle-less injector of the present invention is designed to deliver the medicament intramuscularly, intradermally or subcutaneously to the human or animal. An intramuscular injection is one that passes through the skin and subcutaneous tissue and penetrates the underlying skeletal muscle. A subcutaneous injection is one that fully penetrates the skin and is retained in the space between the skin and the underlying musculature. An intradermal injection floods the epidermal and dermal layers with fluid but does not travel as deep as a subcutaneous injection. There are many reasons why drug delivery to a particular location is important, for example, speed of absorption, decreased side-effects, decreased pain, etc. Moreover, some vaccines are formulated to be delivered to the intramuscular area of the body, some are formulated for subcutaneous and others can be administered to both areas and others are targeted to the dentritic cells of the skin.

Figure 1:
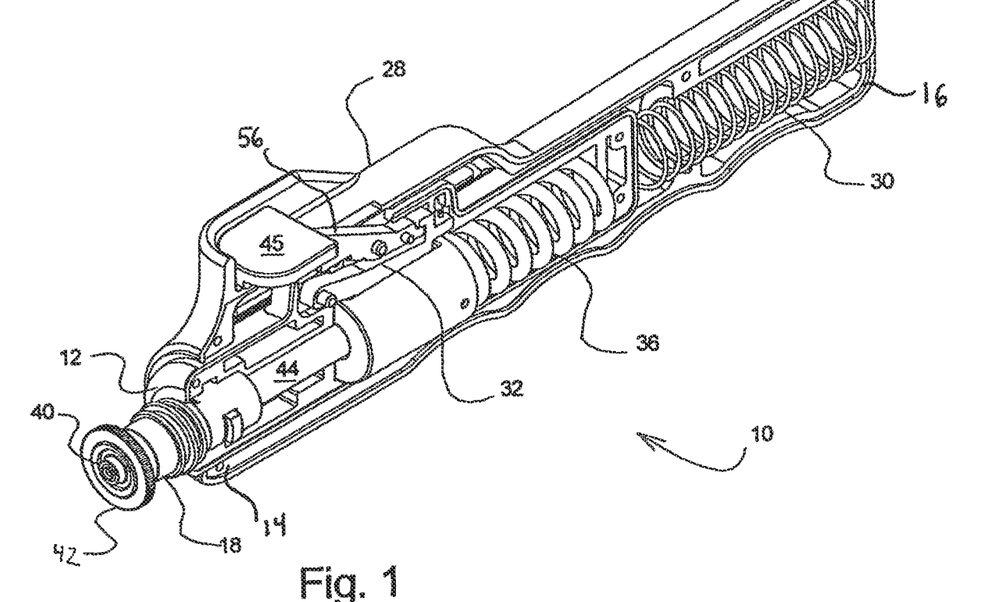
FIG. 1 is a partial cutaway of the needless injector device of the present invention.
Figure 2:
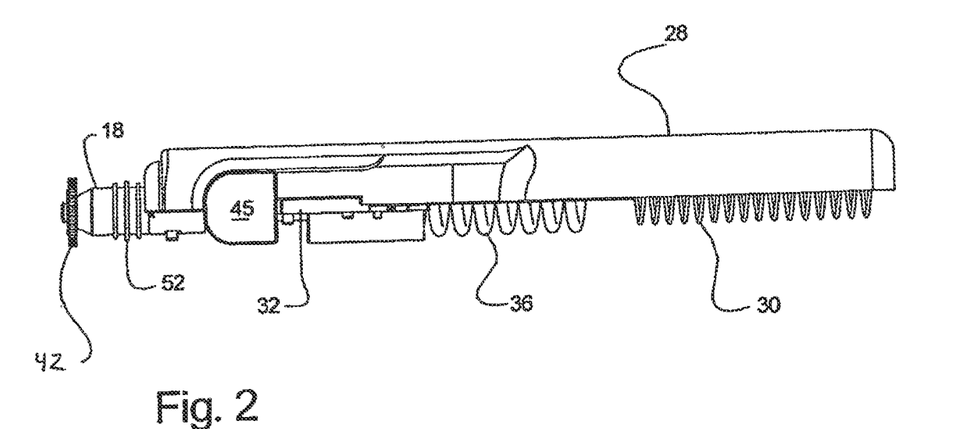
FIG. 2 is a top view of the device of FIG. 1.
Figure 3:
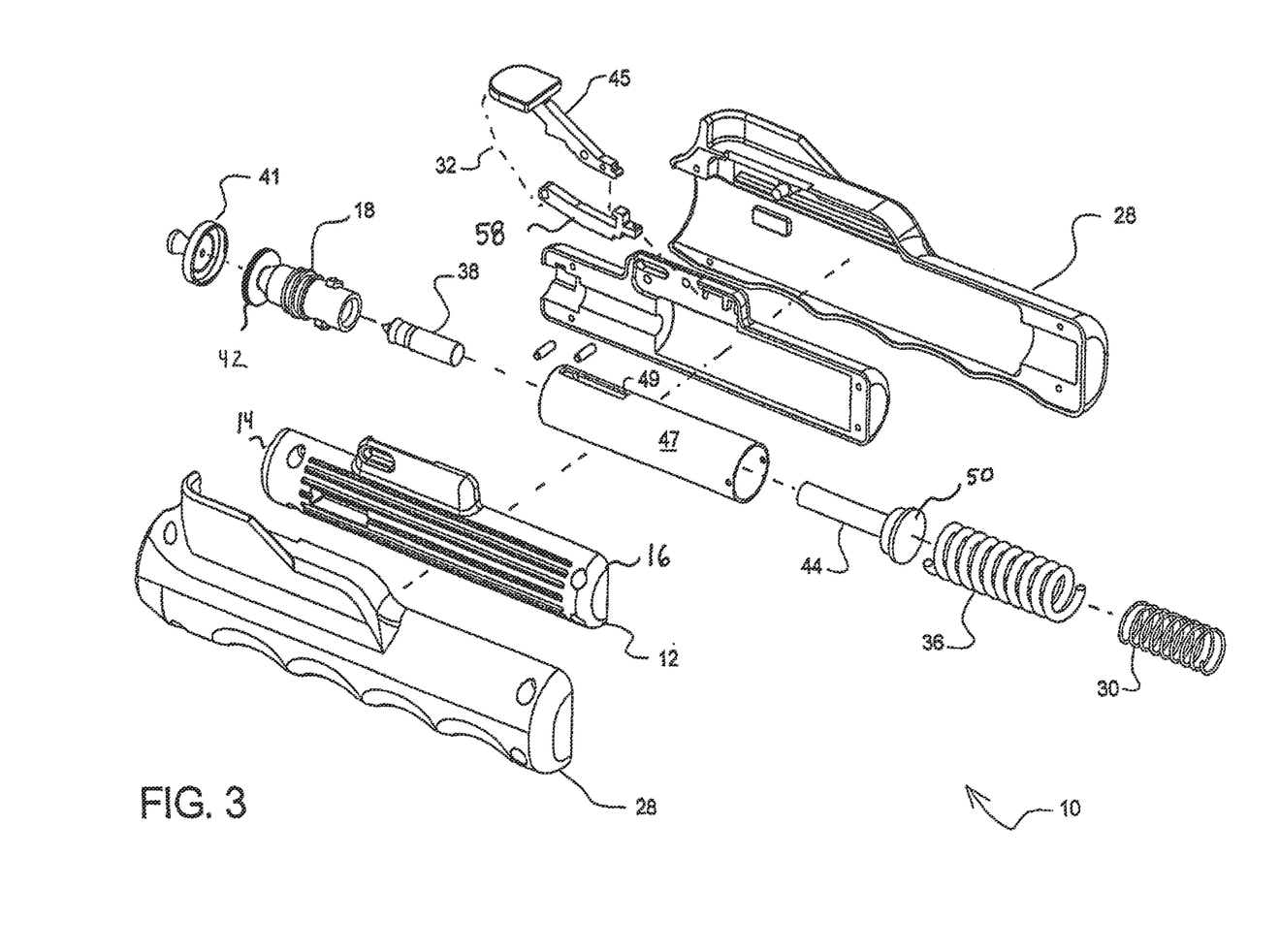
FIG. 3 is an exploded view of the needless injector device of the present invention.

As shown in FIGS. 1-3, inner housing 12 is movably mounted within an outer housing 28 so as to slide along the axial direction thereof. The inner housing is movable from a ready position, illustrated in FIG. 4, to a firing position, sequentially illustrated in FIGS. 5-7.

Figure 4:
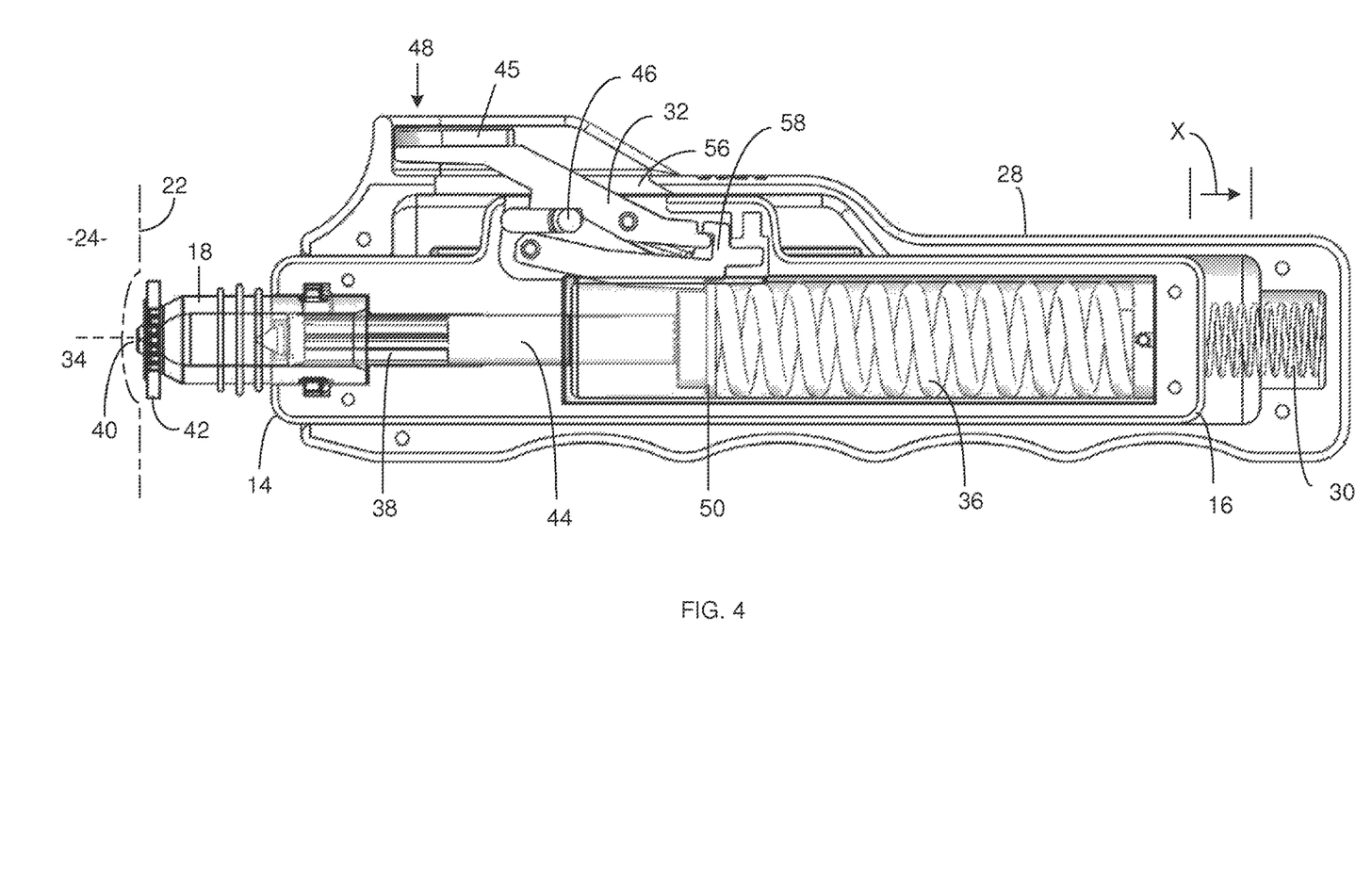
FIG. 4 is a cross-sectional view of the needless injector device shown in the ready position, prior to moving the inner housing into the firing position.

Inner housing 12 can be moved into the ready position of FIG. 4 by a skin tensioning spring 30 that is mounted between the inner housing 12 and the outer housing 28. The skin tensioning spring 30 has numerous functions. One function of spring 30 is to cooperate with the structure of the syringe 18 to pull the animal's skin 22 taut while positioning the skin 22 prior to delivering the fluid 20 into the animal or human tissue 24. Another function of the skin tensioning spring 30 is to cooperate with a trigger mechanism 32 to ensure that the device 10 cannot be fired until the device 10 is properly positioned against the skin 22 covering the tissue of the animal or human 24, and the proper amount of pressure or force exists between the syringe 18 and the skin 22.

The amount of force required to be applied against the skin varies depending on the physical characteristics of the patient or animal being injected with the device 10, as well as the location of the delivery. For example, a mature adult may require higher force to hold the skin taut and penetrate the skin as compared to a child or infant, simply due to the effects of aging on the elasticity of the skin. Likewise, in an animal, it can be more difficult to inject the tougher skin surrounding the back or neck. Accordingly, it is contemplated that the disclosed invention can be manufactured with different skin-tensioning springs, each skin tensioning spring 30 being of a stiffness that is appropriate for a particular application. It is further contemplated that the force imposed by the skin tensioning spring may be made adjustable, for example by adding a threaded plug 33 that screws against the spring 30 to add pre-tension.

The amount of pressure or force that is used to hold syringe 18 against skin 22 is an important variable in the injection process. Needle-less injection devices are capable of delivering fluids through the skin 22 of the animal or human 24 by injecting a jet of fluid 34 into the skin 22 at a sufficiently high pressure and velocity so that fluid jet 34 penetrates through the skin 22 and into the tissue of the animal or human 24.

Important factors that contribute to the device's ability to accomplish the task of forming a jet of fluid 34 are the amount of energy that can be quickly and efficiently transferred to the fluid jet 34, and the device's ability to position the fluid jet 34 such that the energy of the jet is efficiently used to penetrate the tissue.

The energy to be transferred to fluid 20 is stored in an injection delivery spring 36 that drives a plunger and seal 38 into the syringe 18 in order to force the fluid 20 through a nozzle 40 (FIG. 1) that forms the jet of fluid 34, as will be described more fully herein. Injection delivery spring 36 is positioned between a head 50 (FIG. 3) of a hammer 44 and the trailing end 16 of inner housing 12.

In order to obtain the most efficient delivery of the jet of fluid 34 into the skin 22 the nozzle 40 should be positioned at a right angle relative to the skin 22 as the jet of fluid 34 is delivered. Although the device may still operate at other angles, delivering the jet of fluid 34 at some angle other than a right angle could result in a component of the force with which the jet of fluid strikes the skin could be parallel to the skin rather than into the skin 22.

The stiffness of the skin-tensioning spring 30 is selected such that the appropriate amount of force is imposed against the skin 22 of the animal or human 24. The stiffness of the skin-tensioning spring 30 is calculated from the well-known formula:

$$F = k^* x,$$

where F is the required force at the firing position, x is the distance of travel (FIG. 4) of the inner housing 12 relative to the outer housing 28 to position the device in the firing position (where the protrusion 46 does not impede movement of the trigger mechanism 32), and k is the spring constant of the skin-tension spring 30.

Although, the present invention is described in particular to positioning the device directly against the skin, it should be appreciated that the above parameters can be chosen to deliver the jet of fluid through the fabric of a patient. For example, in the case of a pandemic outbreak or a terrorist attack, the medicament can be delivered directly to the patient without the need to remove potentially protective clothing. Also, in the application of a resuscitation agent, the device of the present invention could be used by emergency medical personnel to quickly deliver the resuscitation agent directly through the patient's clothing without the need to take the potentially life threatening time to expose the patient's skin For delivery through the skin surface, syringe 18 can include a skin tensioner 42 that surrounds nozzle 40. Skin tensioner 42 can be a disc positioned approximately about the nozzle exit. It should be appreciated that skin tensioner 42 can take other shapes.

Figure 9A:
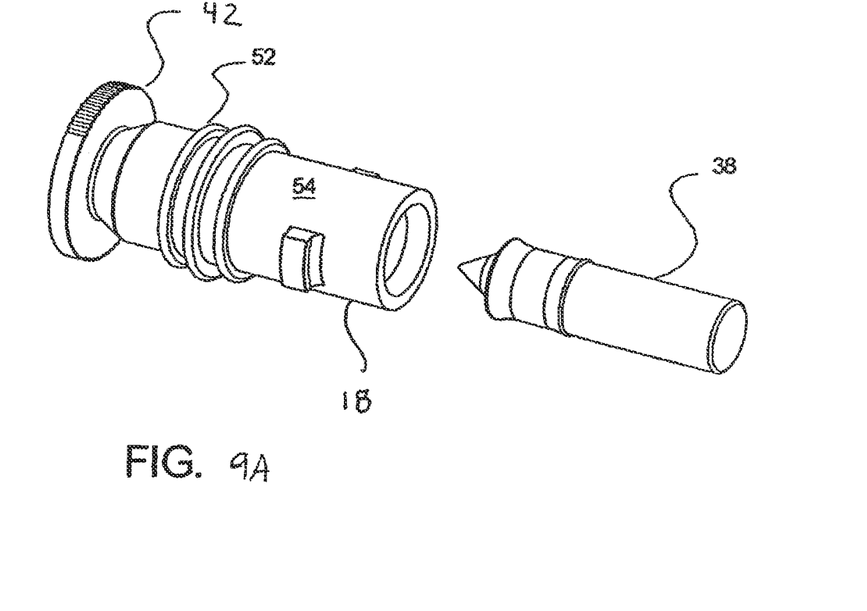
FIG. 9A is a perspective view of an embodiment of the syringe and seal of the present invention.
Figure 9B:
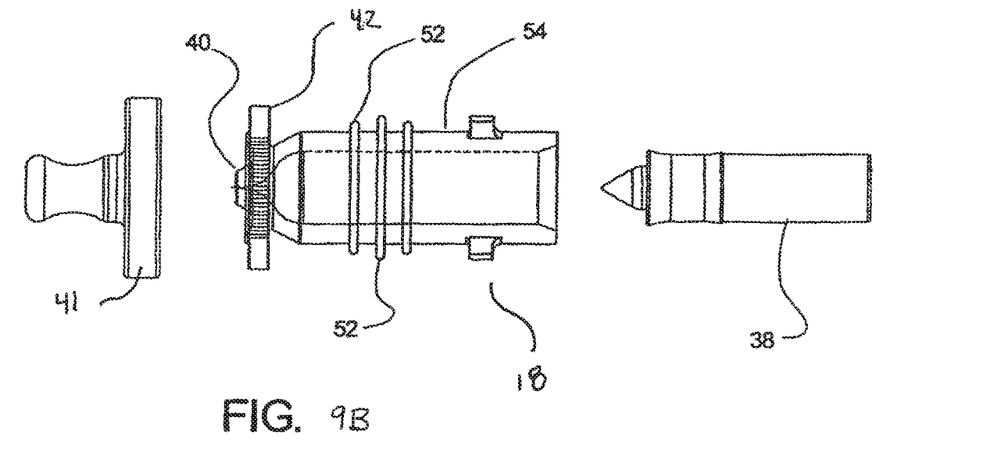
FIG. 9B is a top view of the syringe and seal of FIG. 9A.

As shown in FIGS. 3 and 9B, an installation ring 41 can be provided on syringe 18. The installation ring 41 aids the user in the insertion of syringe 18 into the device 10 and in positioning the device 10 at a right angle to the skin as the jet of fluid 34 is to be delivered. The skin tensioner 42 may cooperate with the installation ring 41 to pull the skin taut as the device is pressed against the skin prior to delivery of the fluid jet 34. It should be appreciated that a certain minimum amount of force must be applied against the skin in order to ensure that the skin is drawn tight prior to the release of the jet of fluid 34.

Referring to FIGS. 1-8, injection delivery spring 36 has opposed ends. One end of spring 36 abuts against the trailing end 16 of the inner housing. The other end of spring 36 abuts against head 50 of hammer 44. Hammer 44 in turn abuts against plunger and seal 38. It should be appreciated that hammer 44 and plunger 38, although illustrated as two separate pieces, can also be formed of a single piece.

Plunger 38 is movably and sealingly disposed in syringe 18. Thus, while plunger 38 can move within the syringe it is sealingly engaged with an inner diameter of the syringe such that the dose of medicament cannot leak therefrom. As shown in FIG. 3, the spring powered hammer 44 rides within a sleeve 47 that includes a slot 49 for accepting latching components of the trigger mechanism 32.

Outer housing 28 includes an aperture 56. A trigger mechanism 32 is mounted in inner housing 12 and protrudes through aperture 56 so as to be engageable by a user. Trigger mechanism 32 includes a trigger 45 and a link 58 that controls the release of hammer 44. As can be understood from comparing the sequential illustrations of FIGS. 4-8, the firing of the device 10 to deliver a dose of fluid is accomplished by pressing the trigger 45 in the direction of arrow 48 after the device 10 is in the firing position, illustrated in FIG. 5. However, the trigger 45 of the trigger mechanism 32 can only release the plunger and seal 38 when the device 10 is in the firing position, illustrated in FIG. 5. When the device 10 is in another position (other than the firing position), such as the ready position of FIG. 4, the trigger link 58 of mechanism 32 cannot be pressed to release the hammer 44. The release of the hammer 44 is prevented for safety and for efficacy of the injection.

Figure 5:
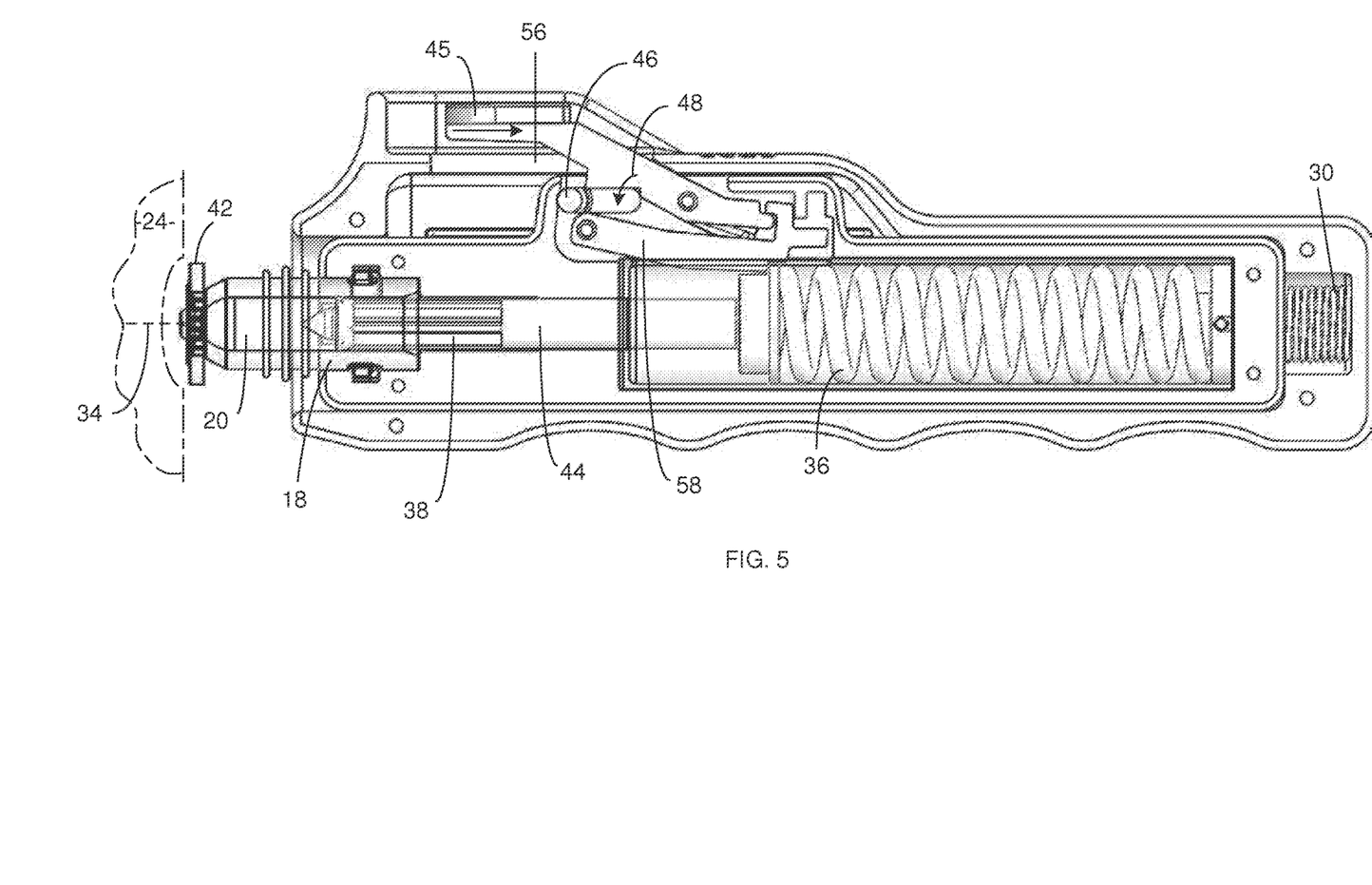
FIGS. 5-7 are a cross-sectional view of the needless injector device of the present invention in the sequential firing positions.
Figure 6:
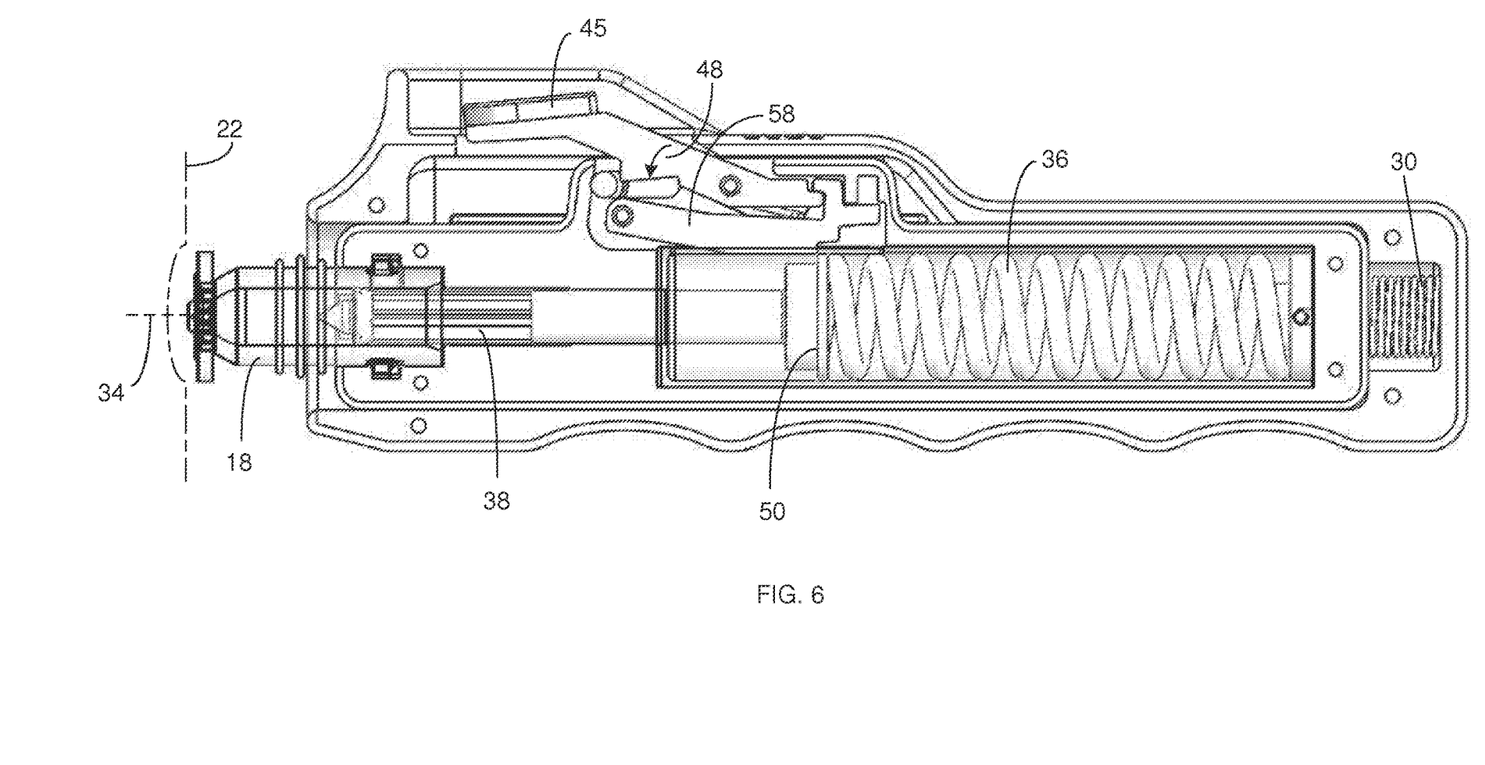
Figure 7:
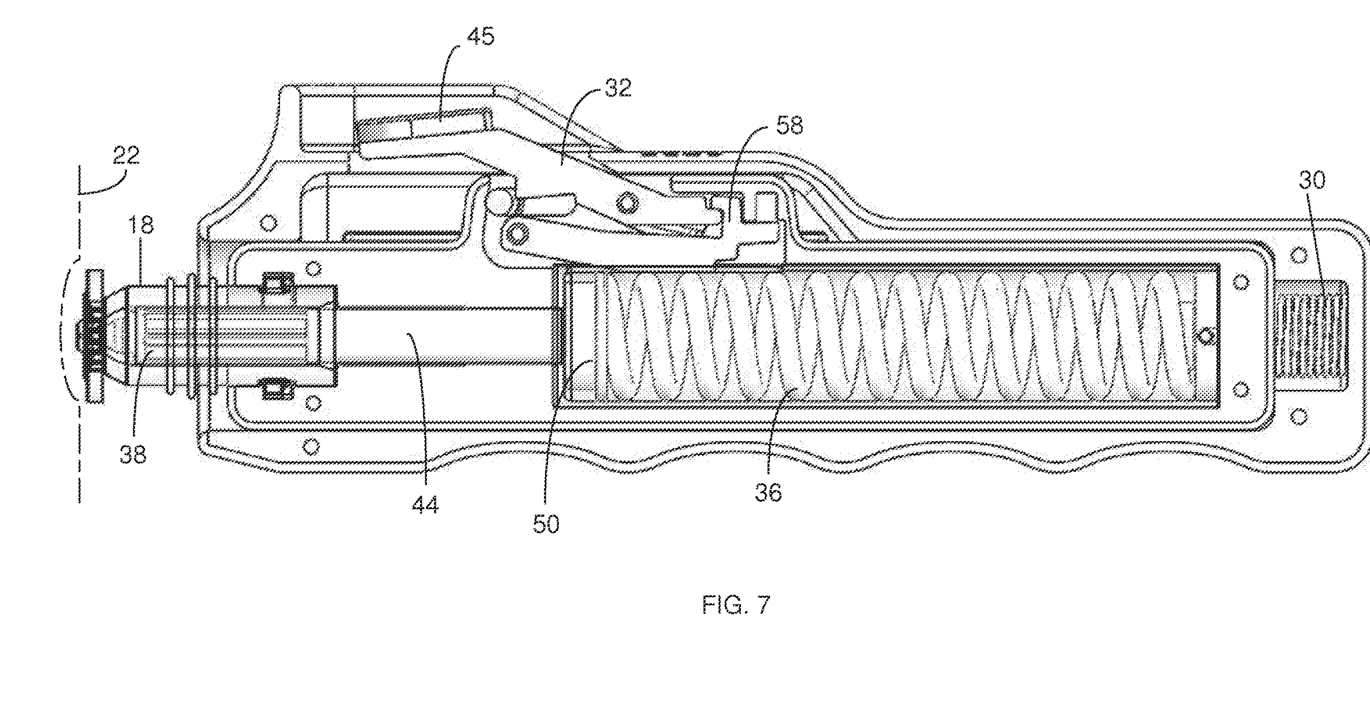
Figure 8:
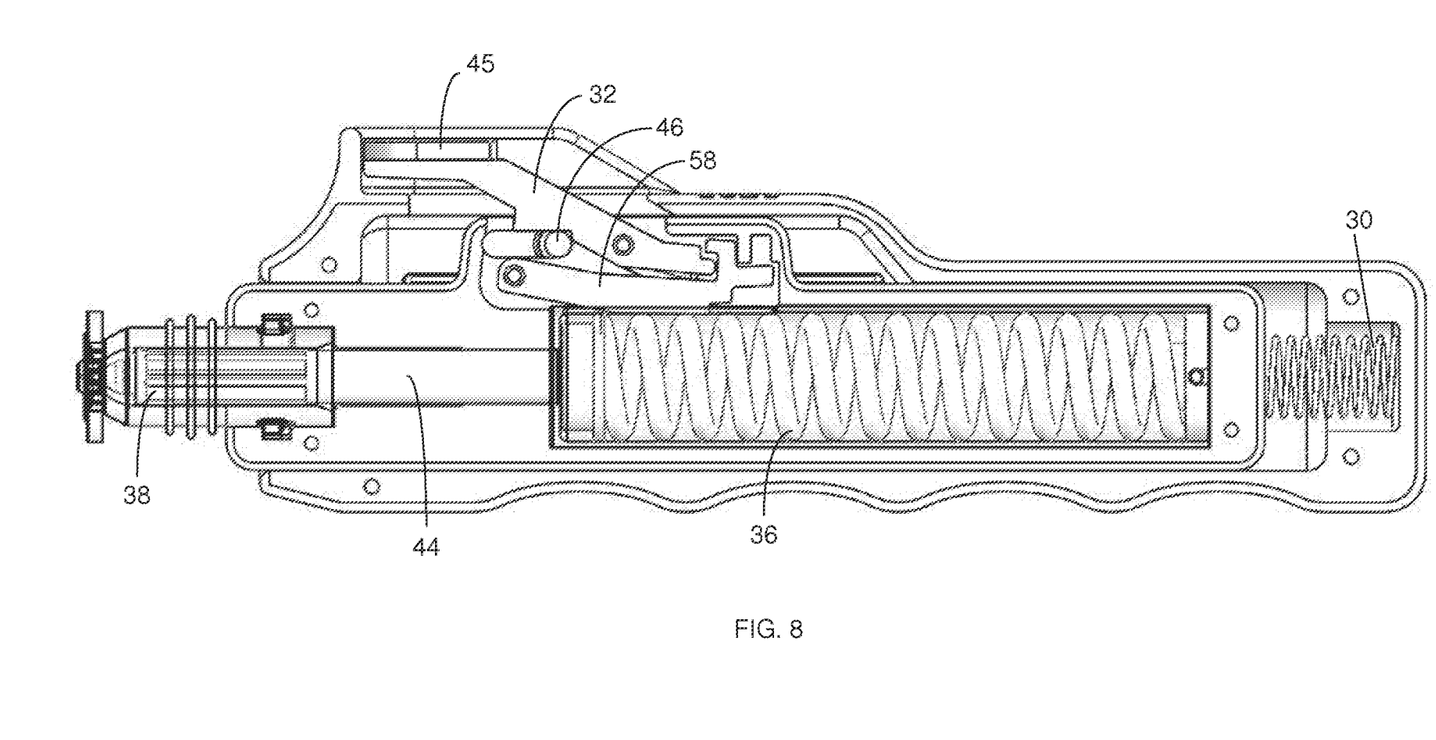
FIG. 8 is a cross-sectional view of the needless injector device of the present invention in a post-injection position.

The unwanted activation of the trigger mechanism 32 is accomplished by positioning a protrusion 46 below trigger 45. The protrusion 46 prevents movement of the trigger 45 in the direction of arrow 48, preventing the release of hammer 44, and thus preventing the firing of the device 10. According to a preferred embodiment of the invention the protrusion 46 extends from the outer housing 28 to a location under the trigger 45. The protrusion 46 is positioned such that it interferes with the movement of the trigger 45 until the device 10 is in the firing positions, as illustrated in FIG. 5-7. After firing, the trigger 45 will be returned to its original position (FIG. 8).

In the preferred example of the invention, the movement of the inner housing 12 relative to the outer housing 28 moves the position of the trigger 45 (which is mounted from the inner housing 12) relative to the outer housing 28, which holds the protrusion 46. The amount of movement of the outer housing 28 relative to the inner housing 12 is accomplished against the force of the skin-tensioning spring 30.

As shown in FIG. 6, once the inner housing 12 is positioned relative to the outer housing 28 such that the desired amount of skin tensioning force is applied to the skin 22 against the syringe 18, which also positions the device in the firing position, the pressing of the trigger 45 causes the release of the spring powered hammer 44 from the cocked position. When the trigger is released, injection delivery spring 36 that has been manually compressed and latched to temporarily store the energy until it is required fire the injector.

Referring to FIG. 7, when the trigger mechanism is pressed, spring 36 is released and hammer 44 is propelled against plunger 38 located in the syringe, vial or ampule 18. The hammer drives plunger 38 against the medicament, producing a high pressured jet for injection purposes. The plunger expels the medicament from a discharge orifice of nozzle 40 and into the patient's skin, muscle and/or subcutaneous tissue.

The initial high pressure discharge causes the jet stream to pierce the skin with the initial injection of the medicament. After a short travel, the expansion of injection delivery spring 36 is completed and the continued movement of hammer 44 and the movement of plunger 38 into the syringe is driven by tensioning spring 30 (FIG. 8). This movement continues the ejection of the jet of medicament from syringe 18 through the aperture in the skin created by the initial high intensity burst. Skin-tensioning spring can have a lower stiffness than the injection delivery spring.

Thus, the medicament can be delivered to a predetermined depth beneath the surface, depending upon the magnitude of the pressure. After the minute opening in the skin has been produced, the pressure of the stream is immediately reduced to a lower second stage for completing transfer of the remaining medicament from the syringe.

It is desirable that the needle-less injector of the present invention have adjustments for the delivered volume of the medicament. Injection delivery spring 36 can be chosen from a variety of spring weights to provide different spring pressures and hence different delivery power of the medicament. As discussed above, the present invention is designed so as to offer different locations for the delivery of the medicament—intramuscularly, intradermally or subcutaneously to the human or animal. A spring having a lighter weight will accommodate a smaller dose or a dose to a subject that has thinner skin, whereas a spring having a larger weight can deliver a larger dose of medicament or a dose to a subject with thicker skin. As with the tensioning spring 30, a particular delivery spring 36 can be chosen by the user and be delivered in the packaged injector. Spring weights can range from 850 and above, more particularly, from 850 to 1980. However, spring weights vary in size and strength according to the tissues injected and it should be appreciated that a variety of springs are contemplated by the present invention and the disclosed range is only an example.

Syringe 18 includes the dose of medicament to be delivered. Depending on the type of vaccine and the intended recipient, a particular dose is predetermined by the manufacturer of the medicament or a physician. Typical vaccine dosages range of and about 0.1-1 cc.

However, recent clinical trials have proven that for some vaccines, reducing the amount of vaccine delivered still achieves the desired level of efficacy as a larger dosage. Another manner in which the needless-injector of the present invention can be used to provide custom injections is to deliver smaller doses of the medicament. In order to accommodate different doses of medicament, the length of the hammer 44 can be varied to accommodate a variety of volumes of doses. For example, a longer length hammer causes the plunger to extend further within syringe 18, decreasing the volume of medicament retained in the syringe 18 prior to ejection from the vial 18. The firing of the injector will dispense a smaller amount of medicament in a shorter time than a shorter length hammer, because the plunger will have less of a distance to travel within syringe 18. The present invention contemplates a delivery range of dose of and about 0.1 cc to 1 cc. However, it should be appreciated that other doses are contemplated by the present invention.

Thus, different doses can be accommodated by the present invention without providing different sized syringes. By lengthening hammer 44, the dosage in syringe 18 can be reduced significantly, for example as low as 0.1 cc. This provides a significant cost advantage. Importantly, lower doses also enable smaller animals and infants to be inoculated. By adjusting the length of hammer 44 and providing a particular delivery spring the amount of dosage and the location of delivery can allow for a custom injection. The length of the head of the hammer is increased in proportionately for the stroke. For example, for a 0.1 cc dose, the length of the hammer is increased by ⅘ths of the stroke.

Syringe 18 can include a plurality circumferential stiffening ribs 52 (FIGS. 9A-9B) that extend around a body 54 of syringe 18. These stiffening ribs help reduce the amount of deflection of the body 54 of the syringe 18 during the delivery of an injection.

As discussed above, disposable syringe 18 contains a dose of liquid formulation for delivery. Syringe 18 can be made of a readily injection moldable material, such as a pharmaceutical grade polypropylene or a polymer material. One example of such a polymer material is TOPAS®, manufactured by Ticona Engineering Polymers, a division of Celanese. As discussed above, medical grade materials allow for factory pre-filling without-interaction with the dose as opposed to filing on site just prior to injection.

Typically polypropylene is extremely difficult to engineer because of pressure distortion. However, the design of the plunger, syringe and the resulting seal of the present invention overcomes previous manufacturing difficulties.

Figures 10, 11:
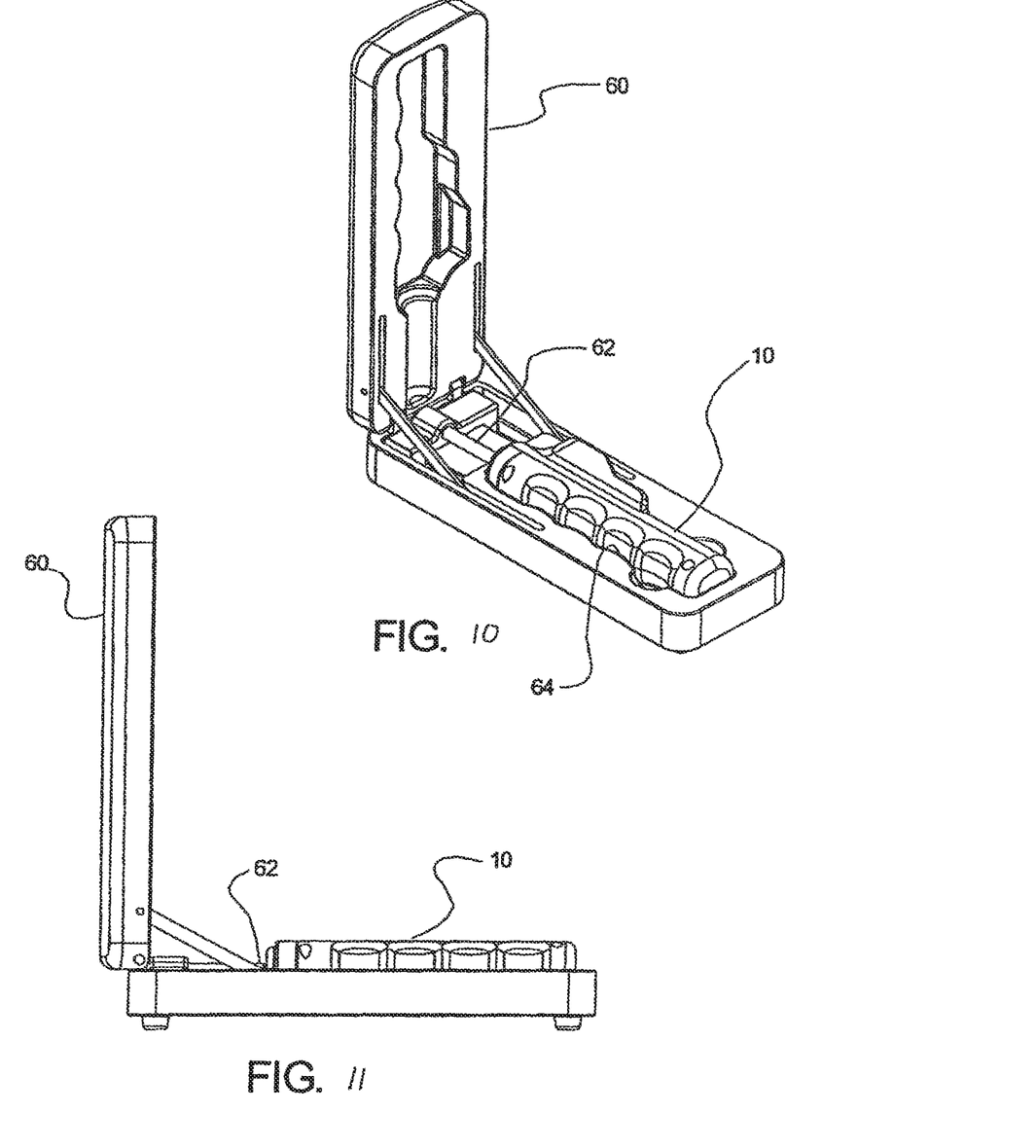
FIG. 10 is a perspective view of a carrying and cocking device for the needle-less injection device of the present invention.
FIG. 11 is a side view of the carrying and cocking device of FIG. 7.
Figure 12:
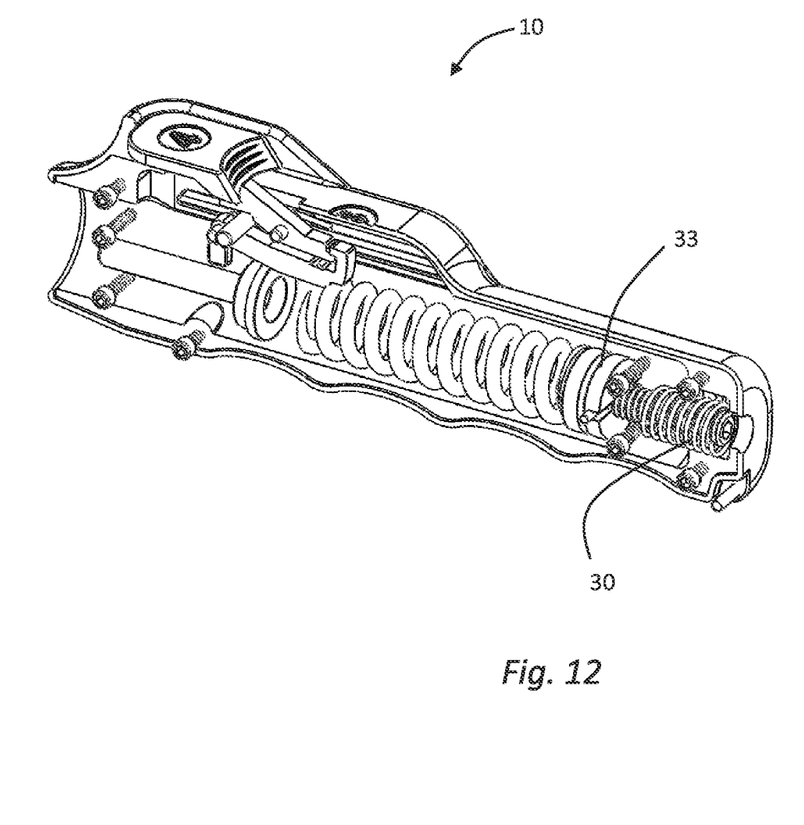
FIG. 12 is a rear isometric cross-sectional view of the adjustable needless injector device.

Referring to FIGS. 10 and 11, it should be understood that the disclosed needle-less injection device can be used with a combined cocking and carrying device 60. The cocking and carrying device includes a cocking hammer 62 that is used to push the spring powered hammer 44 back to the "ready" position shown in FIG. 4. The cocking and carrying device 60 also includes a cradle 64 that retains the outer housing 28 while the cocking hammer 62 is pushed against the spring powered hammer 44.

Cocking hammer 62, when pushed against spring powered hammer 44, moves the hammer into the "ready" position illustrated in FIG. 4. It should be understood that the cocking and carrying device 60 will cock the needle-less injection device 10 once the device is positioned in the cradle 64 and the cocking and carrying device 60 is closed. Thus, device 60 will serve as both a cocking device and case for transporting and storing the needle-less injection device 10.

In operation, depending on the end use, the user selects an injection device with the appropriate skin pre-tension spring 30, injection delivery spring 36, and hammer length. Syringe 18 contains the desired amount of fluid to be delivered into the skin, muscle or tissue of the animal or human. The syringe 18 will be inserted into the leading end 14 of the inner housing 12, preferably through the use of a bayonet-type connector, and mated to a seal that may be a part of the plunger and seal 38.

The outer housing 28 and a cocking and storage mechanism (FIGS. 10 and 11) for use with the device 10 will be color coded to inform the user of the inner spring power, i.e., the injection power, for that particular injector device 10.

The variation of the skin pre-tension spring 30, hammer length and injection delivery spring 36 allows the needle-less injector device 10 to be tailored for a particular application. For example, a needle-less injector device 10 for use on a child would have one particular combination of skin pre-tension spring 30, hammer length and injection delivery spring 36, while the combination of skin pre-tension spring 30 and injection delivery spring 36 for an adult male would likely be a different combination. Accordingly, the disclosed invention can the adapted for use on a variety of animals or humans, and for the delivery of a variety of types injections or depth of delivery of the fluid by varying the skin pre-tension spring 30 and injection delivery spring 36.

As described above, the user will press the face of the syringe against the skin, or fabric, and depress the trigger to give the injection. The injector inner housing slides inside the outer housings, which creates an interlock so that the device cannot be operated until the proper tension against the skin is established. When the trigger is pressed, the trigger latch will release the hammer and the hammer will move the syringe seal into the syringe. The main pressure spring will deliver enough pressure to allow the liquid to pierce the skin.

After the injection has taken place, the syringe is removed and discarded. With a single dose injector because of the tight seal between the plunger and syringe, the syringe is not reusable. The injector is then placed into the cocking mechanism and reloaded for the next injection.

The syringe and seal assembly can be pre-filled or field filled with the use of an adapter and a break-away plunger. Thus, syringe 18 can come pre-filled with the desired dose and type of vaccination and inserted into the injector. Although the above has been described for the use of a fixed dosage, it should also be appreciated that a multi-dose syringe/injector is also contemplated by the present invention. The end of the syringe is constructed such that it can be coupled with a field-filling adaptor to download on-site medicaments from a single dose or multi-dose vial or secondary drug-container.

The syringe of the present invention is also constructed and arranged in such a manner that the drug within the syringe can be lyophilized so that is can be rehydrated with an adjuvant or saline using the filed filling adaptor of co-pending U.S. patent application Ser. No. 11/453,249, the subject matter of which is herein incorporated by reference. In other words, an adjuvant or saline can be downloaded into the syringe of the present invention that is filled with a lyophilized product and rehydrated.

Although the present invention has been described in relation to particular embodiments thereof, many other variations and modifications and other uses will become apparent to those skilled in the art. It is preferred therefore, that the present invention be limited not by the specific disclosure herein, but only by the appended claims.

What is claimed is:

1. A method of providing a needle-less injector comprising:
 assembling a needle-less injector by steps comprising;
  providing an inner housing;
  providing an outer housing;
  positioning the inner housing within the outer housing such that the inner housing is axially movable within the outer housing between a ready position and a firing position;
  receiving input from a user selecting a delivery spring weight from a plurality of available delivery spring weights;
  positioning a delivery spring having the selected delivery spring weight within the inner housing; and delivering to the user the needle-less injector including the delivery spring.

2. The method of claim 1 further comprising placing an indicia on the outer housing indicating the delivery spring weight.

3. The method of claim 2 further comprising placing color coding on the outer housing indicating the delivery spring weight.

4. The method of claim 1 wherein the step of receiving input comprises the user selecting a first alternative delivery spring weight from the plurality of available delivery spring weights, wherein the first alternative delivery spring weight is determined to cause an injection into an intradermal tissue layer.

5. The method of claim 1 wherein the step of receiving input comprises the user selecting of a second alternative delivery spring weight from the plurality of available delivery spring weights, wherein the second alternative delivery spring weight is determined to cause an injection into an intramuscular tissue layer.

6. The method of claim 1 wherein the step of receiving input comprises the user selecting a third alternative delivery spring weight from the plurality of available delivery spring weights, wherein the third alternative delivery spring weight is determined to cause an injection into a subcutaneous tissue layer.

7. The method of claim 1 wherein the step of receiving input comprises the user selecting a fourth alternative delivery spring weight from the plurality of available delivery spring weights, wherein the fourth alternative delivery spring weight is determined to cause an injection having a specific dosage.

8. The method of claim 1 further comprising:
receiving input from the user selecting a hammer length from a plurality of available hammer lengths;
positioning a hammer having the selected hammer length within the inner housing; and
delivering to the user the needle-less injector including the hammer and the delivery spring.

9. The method of claim 8 wherein the step of receiving input comprises the user selecting a first alternative hammer length from the plurality of available hammer lengths, wherein the first alternative hammer length is determined to cause an injection having a first dosage.

10. The method of claim 8 wherein the step of receiving input comprises the user selecting a second alternative hammer length from the plurality of available hammer lengths, wherein the second alternative hammer length is determined to cause an injection having a second dosage.

11. The method of claim 1 further comprising:
receiving input from the user selecting a skin tensioning spring weight from a plurality of available skin tensioning spring weights;
positioning a skin tensioning spring having the selected skin tensioning spring weight between the inner housing and the outer housing to bias the outer housing toward the ready position; and
delivering to the user the needle-less injector having the skin tensioning spring and the delivery spring.

12. The method of claim 11 further comprising:
receiving input from the user selecting a hammer length from a plurality of available hammer lengths;
positioning a hammer having the selected hammer length within the inner housing; and
delivering to the user the needle-less injector having the hammer, the skin tensioning spring, and the delivery spring.

* * * * *